United States Patent [19]

Down et al.

[11] Patent Number: 5,512,440
[45] Date of Patent: *Apr. 30, 1996

[54] PROCESS FOR LYSING MYCOBACTERIA

[75] Inventors: James A. Down, Cary, N.C.; William E. Keating; Adriann J. Walters, both of Baltimore, Md.; Jillian A. Robson, Pittsboro, N.C.; Allen Reichler, Owings Mills, Md.

[73] Assignee: Becton Dickinson and Company, Franklin Lakes, N.J.

[ * ] Notice: The term of this patent shall not extend beyond the expiration date of Pat. No. 5,376,527.

[21] Appl. No.: 287,734

[22] Filed: Aug. 9, 1994

Related U.S. Application Data

[63] Continuation-in-part of Ser. No. 10,467, Jan. 28, 1993, Pat. No. 5,376,527, which is a continuation of Ser. No. 809,806, Dec. 18, 1991, abandoned.

[51] Int. Cl.⁶ .............. C12Q 1/68; C12P 19/34; C12N 1/06
[52] U.S. Cl. .............. 435/6; 435/91.2; 435/259
[58] Field of Search .............. 435/6, 91.2, 253.1, 435/259

[56] References Cited

U.S. PATENT DOCUMENTS 5,376,527  12/1994  Robson et al. .............. 435/6

OTHER PUBLICATIONS

Kolk et al, "Detection of *Mycobacterium tuberculosis* in Clinical Samples by Using Polymerase Chain Reaction and a Nonradioactive Detection System," J. of Clinical Microbiology, 30: 2567–2575, 1992.

*Primary Examiner*—W. Gary Jones
*Assistant Examiner*—Dianne Rees
*Attorney, Agent, or Firm*—David W. Highet

[57] ABSTRACT

The invention provides a rapid process for lysing Mycobacteria. In one embodiment is provided a process for lysing Mycobacteria which comprises exposing the bacteria to a lysis effective amount of heat. A particularly effective method for providing the necessary heat is in the form of forced hot air such as in a forced hot air oven. The process of the invention is particularly advantageous since only one step is involved, it is expedient compared to prior methods, and little instrumentation is necessary. By practicing the present invention it is possible to lyse Mycobacteria with minimal effort. In addition, practicing the invention results in liberating cellular components including deoxyribonucleic acid (DNA) from Mycobacteria. Not only is DNA liberated, but the DNA is suited for subsequent analysis by way of probe hybridization, restriction enzyme analysis, and the like.

26 Claims, No Drawings

PROCESS FOR LYSING MYCOBACTERIA

RELATED DISCLOSURES

This is a continuation-in-part of Ser. No. 08/010,467, filed Jan. 28, 1993, now U.S. Pat. No. 5,376,527, which is a continuation of Ser. No. 07/809,806, filed Dec. 18, 1991, now abandoned.

FIELD OF THE INVENTION

The invention is in the field of molecular biology. In particular the invention is in the area of cell lysis. Most particularly the invention is a process for lysis of Mycobacteria.

BACKGROUND OF THE INVENTION

Mycobacteria are a large, diverse, and widely distributed family of aerobic, nonsporulating, nonmotile bacilli that have a high cell-wall lipid content and a slow growth rate. Members of the Mycobacterium genus vary tremendously in virulence. Some Mycobacteria are harmless while others like *M. tuberculosis* are significant pathogens. Mycobacterium species are differentiated by their growth rate, pigment production, animal virulence, and biochemical reactivity.

Many detection methods for determining the presence of pathogenic organisms such as those in the Mycobacteriaceae family rely on the lysis of those organisms. However, commercial and published lysis procedures for Mycobacteriaceae are expensive, laborious, time consuming and may require caustic reagents, specialized equipment, or both. This contrasts with lysis protocols for other types of cells which generally do not require as stringent conditions for lysis. Recent advances in mycobacterial genetics and increased interest in opportunistic pathogens in patients like those suffering from acquired immunodeficiency syndrome have focused attention to the fact that a procedure for rapid lysis of Mycobacteriaceae is needed. It would be advantageous to have a process for lysing Mycobacteria that is simple, fast, and not disruptive to the material desired from the lysis.

SUMMARY OF THE INVENTION

The present invention provides a process for lysing Mycobacteria that is simple, fast, and not disruptive to the material desired from the lysis. In one embodiment is provided a process for lysing Mycobacteria which consists essentially of exposing the mycobacteria to a lysis effective amount of heat.

Further embodiments include isolating specific cellular components liberated from lysis of Mycobacteria using the process of the invention.

Specific embodiments also include the additional step of isolating nucleic acid from Mycobacteria and amplifying nucleic acid obtained from practicing the process of the present invention.

Other embodiments include the addition of a Mycobacteria identifying agent to the lysed Mycobacteria to identify the presence of Mycobacteria.

The process of the invention is particularly advantageous since only one step is involved, it is expedient compared to prior processes, and little instrumentation is necessary. By practicing the process of the invention it is possible to lyse Mycobacteria with minimal effort. In addition, practicing the invention results in liberating deoxyribonucleic acid (DNA) from Mycobacteria. Not only is DNA liberated, but the DNA liberated is suited for subsequent analysis by way of probe hybridization, restriction enzyme analysis, amplification, and the like.

As used in this document, "lysis effective amount of heat" refers to that amount of elevated temperature which liberates intracellular components such as DNA, RNA, and the like, but which amount does not destroy or render the desired intracellular component unsuitable for subsequent use. In one particularly effective embodiment of the invention, the lysis effective amount of heat is provided as forced hot air.

DETAILED DESCRIPTION OF THE INVENTION

The present invention allows for the lysis and resultant liberation of DNA and cellular material from Mycobacteria.

The heating of Mycobacteria for lysis is advantageous over known methods for lysis of Mycobacteria which involve the use of caustic chemicals, time consuming culturing, and mechanical methods which use the French press, the Hughes press, sonication probes, bath sonicators, freeze-thawing, glass beads, the Ribi pressure cell, and the like (see Table I). The use of heat can kill pathogenic organisms or render such organisms noninfectious, thus simultaneous liberation of intracellular components and rendering of safe samples can be obtained by the process of the invention.

Although numerous enzymes and procedures exist for lysing a variety of organisms, the application of heat to lyse Mycobacteria is unique. Mycobacteria are notorious for their inability to readily lyse. Those procedures that do result in lysis of Mycobacteria also generally destroy the contents of the cell that were desired. If the contents of the cell were not destroyed from the lysis procedure, it was generally the result of timely and laborious protocols. Mycobacteria are extremely resistant to physical stress and can be subjected to concentration and digestion procedures that kill ordinary bacteria (compare Tables I and II). Thus, it is unexpected that heating alone, which can lyse less strenuous bacteria, can also lyse the extraordinarily lysis resistant Mycobacteria. It is also unexpected that heating works so well in lysing Mycobacteria because other, more stringent conditions, do not work. However, the practice of the present invention results in Mycobacteria lysis and subsequent yield of useable pieces of DNA that are suitable for use for a variety of purposes such as detection methods and amplification, as well as liberating RNA and other cellular components. The process of the invention can provide DNA and RNA from the lysed microorganisms in single stranded form.

Tables I and II set forth a substantial number of protocols for lysing mycobacteria, all of which require more involvement than the present invention.

TABLE I

COMMERCIAL AND PUBLISHED METHODS FOR LYSIS OF MYCOBACTERIA

| Author/Source | Method | Reference |
|---|---|---|
| GenProbe | 15' sonication with lysing buffer and glass beads | Gen-Probe package insert |
| Pierre et al (1991) | 15' @ 95° C. with 0.1N NaOH, 2M NaCl, 0.5% SDS | J. Clin. Micro. 29 (4):712–717 |
| Hurley et al (1988) | 3' in minibead beater (Biospec Prod. Bartlesville, OK) with distilled phenol and 0.1-mm zirconium beads | Int. J. Systematic Bacteriology 38(2): 143–146 |
| Labidi | Mycobacteria converted to spheroblasts by growth in 1.4% glycine, 60 ug/ml D-cycloserine, 1 mg/mL lithium chloride, 200 ug/ml lysozyme, 2 mg/mL EDTA; then pelleted by centrifugation and heated 15' @ 65° C. in 1% SDS. | Archs. ·Inst. Pasteur. Tunis. 655(3–4):261–270 |
| Butcher et al (1988) | 3 hr @ 37° C. with 10 mg/ml subtilisin; then 3 hr @ 37° C. with 50 mg/ml lysozyme; then 12 hr @ 37° C. with 3 mg/ml pronase and 1% SDS. | Gut 29:1222–1228. |
| Wayne and Gross (1968) | 72 hr @ 37° C. with vigorous aeration; then 24 hr @ 37° C. anerobically with 10 uM EDTA, 1 mg/ml pronase; then 90' @ 56° C. with 5% DOC. | J. Bacteriol. 95(4): 1481–1482. |
| Brisson-Noel et al (1989) | Culture: 15' @ 95° C. with 0.1M NaOH, 2M NaCl, 0.5% SDS Blood: 4 hr @ 37° C. with 10 mg/ml lysozyme; then 16 hr @ 55° C. with 5 mg/ml pro K and 0.1% Triton X-100. | Lancet, 11/4:1069–1071. |
| De Wit et al | 30' @ 70° C. with 10 mM Tris-HCl, pH 8.5, 1 mM EDTA, 150 mM EDTA; then 3 hr @ 37° C. with buffered phenol: 1.5% SDS (1:1 volume) with orbital shaking. | J. Clin. Micro.28(11):(1990) 2437–2441. |
| Roberts et al (1987) | 3 washes with 0.85% NaCl; then 15' @ 20° C. with 70% ethanol; then –70° C. | J. Clin. Micro 25(7): 1239–1243. |
| Picken et al (1988) | 16 hr @ 37° C. with 100 mg/ 0.8 mL lysozyme; then 1 hr ~37° C. with 1 mg/ml pro K; then 6 hr @ 50° C. with 2% SDS. | Mol. Cell. Probes 2:289–304 |
| Sjobring et al | SDS; then proteins removed by proteinase K; then precipitated with CTAB. | J. Clin. Micro 28(10): 2200–2204. |
| Whipple et al (1987) | 2 hr @ 37° C. with 8000 U/0.5 mL lipase; then 2 hr @ 37° C. with 5 mg/ml lysozyme; then 16 hr @ 50° C. with 2 mg/ml pro K and 1% SDS; then 10 min 0° C. with 0.4 volumes 5M potassium acetate. | J. Clin. Micro. 25(8): 1511–1515. |
| Vary et al (1990) | 3 hr @ 37° C. with 10 mg/ml subtilisin; then 3 hr @ 50° C. with 5 mg/ml lysozyme; then 18 hr with 3 mg/ml pronase and 1% SDS; then 6 hr with fresh 3 mg/ml pronase. | J. Clin. Micro 28(5): 933–937 |
| Eisenach et al (1986) | 24–72 hr with D-cycloserine; 30' @ 37° C. with 1 mg/ml lysozyme in 15% sucrose, 50 mM Tris-HCl, 50 mM EDTA; then 10' @ 25° C. with 0.1 mg/ml pro K; then 2 hr @ 37° C. with 1% SDS. | Am. Rev. Resp. Dis. 133 1065–1068 |
| Patel et al (1986) | 15' in light petroleum: chloroform:buffer (3:1:1) with vortexing and mixing; then centrifugation; then 2–4 hrs @ 37° C. with 10 mg/ml nagarase; then 2–4 hr @ 50° C. | J. Gen Micro. 132:541–551 |

TABLE I-continued

COMMERCIAL AND PUBLISHED METHODS FOR LYSIS OF MYCOBACTERIA

| Author/Source | Method | Reference |
|---|---|---|
| | with 50 mg/ml lysozyme; then 12–36 hr @ 37° C. with 1% SDS and 3 mg/ml pronase added @ 12 hr intervals. | |
| Pao, et al | 30' @ 37° C. with 2 mg/ml lysozyme in 25% sucrose, 0.1 M EDTA, 50 mM Tris-HCl; then 0.1% SDS in 0.1M Tris-HCl, 0.1M NaCl. | Tubercle 69:27–36. |
| Visuvanathan et al (1989) | 1 hr @ 70° C.; then 18 hr @ 37° C. with about 12.5 mg/ml subtilisin; then 5 hr @ 50° C. with about .31 mg/ml lysozyme; then 12 hr with about 2% SDS and 3 mg/ml pronase; then 8 hr with fresh 3 mg/ml pronase. | J. Micro. Methods 10:59–64. |
| Sritharin and Barker (1991) | NALC pellets suspended in 10 mM Tris-HCl, pH 8.0, 1 mM EDTA and 1% Triton X-100 and boiled for 30 min. | Mol. Cell. Probes 5:385–395 |
| Kolk et al (1992) | NALC pellets subjected to digestion buffer of 5% Tween 20 and 10 mg/ml proteinase K and boiled for 15 min. | J. Clin. Micro. 30: 2567–2575 |
| Victor et al. (1992) | NALC pellets centrifuged and vortexed | J. Clin. Micro. 30:1514–1517 |
| Shawar et al. (1993) | NALC pellets subjected to lysis buffer of 10 mM Tris HCl, 1 mM EDTA and 1% Triton X-100 and boiled for 30 min. | J. Clin. Micro. 31: 61–65 |
| Plikaytis et al. (1991) | NALC pellets suspended in buffer containing 20 mg/ml lysozyme; 0.5M NaOH and 1% SDS added and boiled for 5 min. | Am. Rev. Respir. Dis. 144:1160–1163 |
| Cousins et al. (1992) | NALC pellets heated at 75° C. for 45 min. and lysed with 2 mg/ml lysozyme, 1% SDS and 100 ug/ml proteinase K | J. Clin. Micro. 30:255–258 |
| Del Portillo et al. (1991) | sputum diluted in $H_2O$ and boiled for 10 min., then incubated at 37° C. in 2 mg/ml lysozyme, and 1% SDS and 250 ug/uL proteinase K added before incubating at 65° C. for 20 min. | J. Clin. Micro. 29:2163–2168 |
| Buck et al. (1992) | NALC pellets of clinical samples centrifuged at 16,000 × g for 10 min., then sonicated for 30 min., and boiled for 10 min. | J. Clin. Micro. 30:1331–1334 |
| Savic et al. (1992) | samples liquified and pelleted by sputolysin procedure; pellets boiled for 10 min., mixed with glass beads, incubated with 40 ug proteinase K and 0.5% Tween 20 at 37° C. for 30 min and sonicated at 60° C. for 20 min. | J. Inf. Dis. 166:1177–1180 |
| Shankar et al. | sample centrifuged and pellet subjected to 0.1N NaOH, 1M NaCl and 0.5% SDS, then heated at 95° C. for 15 min. | Lancet 33:5–7 |
| Pierre et al. (1991) | samples liquified and pelleted by SDS procedure, then pellets incubated with 0.1N NaOH, 2M NaCl and 0.5% SDS at 95° C. for 15 min. | J. Clin. Micro. 29:712–717 |
| Thierry et al. (1992) | same as Pierre et al 1991 above | Mol. Cell. Probes 6:181–191 |
| Brisson-Noel et al. (1989) | same as Pierre et al. 1989 above | Lancet, Nov. 4 1069–1071 |
| DeWit et al. (1990) | pleural fluid mixed with polyethylene glycol (PEG), centrifuged and pellet extracted for 3 hours at 37° C. with 10% SDS, buffered phenol. | J. Clin. Micro. 28:2437–2441 |
| Sjoborg et al. (1990) | samples liquified and pelleted by sputolysin procedure; pellet sus- | J. Clin. Micro. 28:2200–2204 |

TABLE I-continued

COMMERCIAL AND PUBLISHED METHODS FOR LYSIS OF MYCOBACTERIA

| Author/Source | Method | Reference |
|---|---|---|
| | pended in 50 mM Tris, boiled for 5 min. and sonicated with glass beads at 50° C. for 15 min. | |

Legend:
SDS, sodium dodecyl sulfate;
CTAB, cetyl trimethyl ammonium bromide;
pro K, proteinase K;
Tris-HCl, Tris(hydroxymethyl) aminomethane hydrochloride;
EDTA, ethylene diamine tetraacetic acid.

TABLE II

Examples of Published Lysis Protocols for Nonmycobacterial Cells

| Author/Sample | Method | Reference |
|---|---|---|
| deKloet/yeast | 1' @ 32° C. with 20 U/ml lyticase | J. Micro Meth. 2:189–196 |
| Monsen et al/ streptococci (1983) | 5–60' @ 37° C. with 0.1 mg/ml mutanolysin in 5 mM EDTA, 0.5% Triton X-100 | FEMS Micro. letters 16:19–24. |
| Chassy/gram+ Gluffrida bacteria (1980) | 60' @ 37° C. with 1.2 mg lysozyme per 1.0 mg bacterial cells | Appl. Env. Microbiol. 39(1):153–158. |
| Gross–/mammalian Ballard et al | 12 hr @ 37° C. with 50 mg/ml pro K. | Eur. J: Biochem. 36:32–38 |
| Grimberg/blood et al cell (1989) nucleii | 2 hr @ 37° C. with 1 mg/ml pro K in 10 mM Tris-HCL, 10 mM NaCl, 10 mM EDTA | Nucleic Acids Res. 17(20):8390 |
| Moreno/blood et al (1989) | 1 hr @ 50° C. with 200 ug pro K in 0.4M Tris-HCl, 0.1M EDTA, 1% SDS | Nucleic Acids Res. 17(20):8393 |
| Birnboim &/E. coli Doly (1979) | 30' @ 0° C. with 2 mg/ml lysozyme; then 5' @ 0° C. with 0.2N NaOH, 1% SDS | Nucleic Acids Res. 7(6):1513–1523 |
| Klein/E. coli et al (1980) | 15' @ 20° C. with 1 mg/ml lysozyme in 10 mM Tris-HCl. | Plasmid 3:88–91 |

Subsequent use of cellular components liberated from lysis include identification of Mycobacteria and amplification of nucleic acid by means such as polymerase chain reaction, Strand Displacement Amplification (SDA), ligase chain reaction, and the like. Identification can take place by means of Mycobacteria identifying agents. Identifying agents refers to those agents suitable for identifying Mycobacteria which include nucleic acid probes including deoxyribonucleic acid and ribonucleic acid, and the like.

The use of probes, for example, for identifying the presence of a particular Mycobacterium can be employed in a one step identification method. For example, once a sample is obtained, heat is applied to the sample, followed by the addition of an identifying agent. If the sample is a sputum sample, the sample is first digested with liquifying agents like N-Acetyl-L-Cysteine (NALC) and sodium hydroxide. The presence of Mycobacteria can then be detected by a variety of means, depending on the marker (e.g., signal to be detected) chosen for use with the identifying agent. The means for identification of the presence of Mycobacteria is usually dictated by the identifying agent employed. For example, nucleic acid probes (e.g., specific for a Mycobacteria species) are typically labeled with $^{125}$I, $^{32}$P, fluorescent dyes, chemiluminescent or colorimetric enzymes and the like. The marker is then detected, which detection is an indication that the particular Mycobacteria is present. Other means for detection include Southern Blot analysis, electrophoretic gel visualization, and the like. The detection can take place with or without prior amplification, depending on the sample and circumstance.

The process of the invention can be employed once the Mycobacteria have been obtained in the form of a sample such as sputum, or an isolated form. Mycobacteria are isolated from a variety of sources including feces, sputum, urine, serum, tissue, other body fluids or obtained from public or private culture collections, and the like. Mycobacteria obtained from the various sources are typically cultured, which is very time consuming, reaching three to six weeks culture time. However, by practicing the method of the invention, the need to culture can be eliminated. If culturing is not desired, the cells are generally first isolated from the source by conventional sample processing methods then usually pelleted by centrifugation and put into a cell suspension. The Mycobacteria in the cell suspension are then subjected to heat.

The ability to use the process of the invention with a clinical sample is particularly advantageous. The organism from which intracellular components are desired is typically subjected to heat in the range of about 60° C, to about 100° C. The heat range for a particular organism is readily obtainable by titrating heat within this range against release of desired target molecule from the organism. The heat will lyse the organism with subsequent release of intracellular components. The only limitation on the use of heating is that the particular intracellular component of interest not be susceptible to destruction by the heat. Therefore, intracellular components that are not destroyed by the heat employed to release the components may be obtained by using the process of the invention. A variety of means for heating with the process of the invention are available. Heating means include water baths, microwaves, convection ovens, forced hot air ovens, and the like.

The process of the invention is particularly beneficial for obtaining DNA or RNA from an organism. The process of the invention allows DNA and RNA to be liberated from organisms in single stranded form. Generally, lysis procedures for obtaining DNA provide the DNA in double stranded form, which form is then subjected to extra steps to obtain single stranded DNA for subsequent use. Thus, the process of the invention provides DNA and RNA in a readily useable form for subsequent use, eliminating the perceived need to use caustic chemical reagents such as sodium hydroxide to obtain single stranded nucleic acid. Most detection and amplification procedures require the DNA and RNA be in single stranded form. A variety of amplification methods are available, for example, Strand Displacement Amplification (SDA), (Walker G. T. et al. *Proc. Natl. Acad. Sci USA* 89, 392 (1992)), polymerase chain reaction (PCR), (PCR Technology, H. A. Erlich, Ed. (Stockton Press, New York, NY 1989)), transcription-based amplification system (TAS), (*Proc. Natl. Acad. Sci. USA* 86:1173 (1989)), ligation amplification reaction (LAR), (*Genomics* 4:560 (1989)), ligase based amplification system (LAS), (*Gene* 89:117 (1990)), and Q B replicase, (*Infect. Dis.* 162:13 (1990)). The goal of any sample preparation is to render the target molecule accessible and improve sensitivity. Such a goal is obtained by taking into account the way samples are prepared, the specific activity of labelled probes, and the selection of a medium or substance in which the sample is prepared.

The heating time required for obtaining intracellular components ranges from about two minutes to about twenty minutes. The amount of heat and time of heat is readily found by sampling a portion of the mycobacteria to be lysed and examining for signs of lysis (e.g., detection of intracellular components), depending on the source from which the intracellular components is to be obtained.

In the most basic embodiment of the invention a sample (clinical sample or cultured sample) containing the intracellular components desired is heated to obtain readily useable components. The organism to be lysed can be in $H_2O$, but also can be in suitable buffers such as Tris-buffered saline (50 mM Tris-HCl, 150 mM NaCl, pH8.0), phosphate-buffered saline (50 mM sodium phosphate, 150 mM NaCl, pH8.0), polymerase chain reaction buffer (10 mM Tris-HCl, pH8.8, 50 mM KCl, 1.5 mM $MgCl_2$), React6 (buffer name React6 is registered by Bethesda Research Labs) (50 mM Tris-HCl, pH7.1, 50 mM NaCl, 50 mM KCl, 6 mM $MgCl_2$), sodium phosphate (pH 5.0 to 12.0), Trizma 9.0 (sigma:Trishydroxyaminomethylamine), and detergents such as 0.5% Tween 20 and 0.5% Nonidet P-40. Optionally the heated sample can be centrifuged, making available the supernatant and pellet for subsequent use.

Once the sample is heated, subsequent use of the intracellular components can include amplification, detection, and the like. Further steps involving the released intracellular components include subsequent purification of the desired component. For example, typical purification steps for obtaining DNA from a lysed sample include organic extractions such as phenol/chloroform extractions or solid phase adsorption onto silica surfaces such as glass or diatoms.

The process of the invention can be practiced without prior culturing. Unpurified biological samples from sputum, feces, tissue, blood, serum, and the like, can be lysed by practicing the invention and in the same sample could be identified with a Mycobacteria identifying agent. Thus the method comprises a simplified means for detecting Mycobacteria in a clinical, biological, food or environmental sample.

A typical protocol for lysing Mycobacteria with heat comprises centrifugation of a sample of Mycobacteria for a brief amount of time (e.g., about five minutes) and discarding the resultant supernatant. The pellet of Mycobacteria can then be reconstituted in a buffered mixture. If required, any suitable buffer will work. After a brief incubation period with a lysis effective amount of heat, the desired intracellular components can be isolated. Conventional methods for isolating DNA include phenol:chloroform extractions, glass binding with subsequent elution, and the like. Examples of conventional protocols for isolating DNA are found in references such as T. Maniatis et al., *Molecular Cloning: A Laboratory Manual* (*Cold Spring Harbor Lab*) (1982) and Boom et al., *J. Clin. Micro* 28:495 (1990).

As stated above, the lysis effective amount of heat can be provided from a variety of sources including water baths, microwaves, convection ovens and forced hot air ovens. However, there are a number of advantages associated with the use of forced hot air ovens including the maintenance of a clean and dry external environment for sample tubes, more efficient and rapid heat transfer than convection ovens and heating blocks, and excellent reproducibility.

In contrast to hot water baths, the forced hot air oven does not produce a wet external surface on sample tubes. Such wet external surfaces are a contributing cause of cross contamination between samples during subsequent processing of the samples. The wet surfaces also render the sample tubes more difficult for a technician or scientist to efficiently handle and manipulate. These same undesirable features of wet external surfaces are present when sample tubes are heated in a heating block with a liquid interface.

In contrast, if the heating block is dry (i.e. without a liquid interface) heat exchange to the sample is slower than with a forced hot air oven, and reproducibility is poor because of a cooler area above the heating block which prevents consistent achievement of consistent temperatures for the samples. Similarly, convection ovens maintain a clean, dry exterior sample tube surface, but display slow heat transfer resulting in long delays before samples reach a desired temperature.

The forced hot air heating of samples eliminates or significantly reduces the foregoing undesirable characteristics of other heating methods by providing rapid production of desired sample temperature, excellent reproducibility of results, and a clean, dry sample tube surface to reduce cross contamination between samples. The quality of temperature control with forced hot air heating is attributable to rapid movement of air around the entirety of the sample tubes.

Forced hot air heating can be achieved with any commercially available forced hot air oven which can achieve a temperature range from ambient to about 150° C. And can preferably go from ambient temperature to a desired temperature of about 100° C. To 105° C. in about two minutes. The velocity of the air moving through the oven is about 3 meters/second to about 6 meters/second. The pattern of the air flow within the oven should be such that all sample tubes are efficiently heated to desired temperature consistently and uniformly. In commercially available forced hot air ovens, the air flow is generally parallel or perpendicular to the tube or container holding the sample, however any air flow pattern or configuration which results is substantially complete immersion of the tube or container in the hot air is acceptable.

In addition, due to the consistency of the heat transfer with forced hot air heating, it has been found that a more consistent loss of viability or killing of mycobacteria occurs. The killing of the mycobacterial organism can be as important as its lysis because of the infectious nature of these organisms. Inconsistency in the killing of mycobacteria presents an unsafe environment for those researchers attempting to lyse mycobacteria to obtain nucleic acid. As explained in greater detail in the Examples, convection ovens and heating blocks do not consistently provide mycobacterial samples which have achieved sufficient temperatures to be rendered noninfectious or killed.

In all of the above-described heating methods, the Mycobacterial sample is held in a closed tube or other container during heating. Thus, the vapor pressure in the tube or container increases with increasing heat in accordance with the relationship between pressure, absolute temperature and volume set forth in Charles Law. A simple manner in which to determine the pressure inside the tube or container is by reference to readily available tables such as those presented in the Handbook of Chemistry and Physics published by the Chemical Rubber Company ("CRC").

Important Mycobacteria that can be lysed by practicing the present invention include *M. avium, M. gordonae, M. tuberculosis, M. kansasii, M. fortuitum, M.chelonae, M. bovis, M. scrofulaceum, M. paratuberculosis, M. marinum, M. simiae, M. szulgai, M. intracellulare, M. xenopi, M. ulcerans, M. leprae, M. lepraemurium, M. smegmatis, M. flavescens, M. terrae, M. nonchromogenicum, M. malmoense, M. asiaticum, M. vaccae, M. gastri, M. triviale., M. haemophilum, M. africanum, M. thermoresistable*, and *M. phlei*. Several of the Mycobacteria are pathogenic. For example, *M. tuberculosis*, which already infects two billion people and infects an additional seven to nine million people each year, is an important Mycobacteria from an epidemiologic and clinical viewpoint In addition, *M. avium, M. bovis, M. intracellularae, M. africanum, M. leprae, M. chelonae, M. paratuberculosis*, and *M. marinum*, are also significant from an epidemiological and clinical viewpoint.

The practice of the present invention provides a rapid and simple lysis procedure for Mycobacteria that provides DNA, RNA and cellular components for subsequent use in a variety of detection procedures.

The following examples illustrate the specific embodiments of the invention described in this document. As would be apparent to skilled artisans, various changes and modifications are possible and are contemplated within the scope of the invention described.

EXAMPLE 1

Purpose:
Initial demonstration of effect of heat alone for *M. tuberculosis* lysis.
Procedure
3 ml pellets of *Mycobacteria tuberculosis* cultures were prepared by culture in 7H10 media in a BACTEC system (Becton Dickinson, Towson, Md.).

The sample was reconstituted in 0.5 ml $H_2O$ then placed in a boiling water bath for 15 minutes.

The lysed sample underwent 2 phenol/chloroform extractions then 2 chloroform/isoamyl alcohol extractions. These were followed by ethanol precipitation overnight at $-20°$ C. Sample was reconstituted in 150 µl $H_2O$. PCR mixes were set up, each using 50 µl the lysate product and then cycled. 10 µl of the PCR product was run on acrylamide gels (10%). 50 µl of the original sample was also used for slot blot hybridization analysis using GENE SCREEN Plus hybridization transfer membrane (DuPont catalogue no. NEF-976) according to the manufacturer's protocol.
Results:
The ethidium stained gel of the PCR product indicated that heating released sufficient target DNA to allow it to be amplified by PCR and detected on the gel. The autoradiogram of the blot showed that DNA had been liberated from the Mycobacteria and had hybridized to the radioactive probe.

EXAMPLE 2

Procedure
3 ml pellets of BACTEC *Mycobacteria tuberculosis* cultures were prepared in substantial accordance with the teachings of Example 1. The sample was reconstituted in 0.5 ml $H_2O$ then sonicated at $60°$ C. for 15 minutes. The lysed sample underwent 2 phenol/chloroform extractions then 2 chloroform/isoamyl alcohol extractions. These were followed by ethanol precipitation overnight at $-20°$ C. Sample was reconstituted in. 150 µl $H_2O$. PCR mixes were set up, each using 50 µl of the lysate product and then cycled. 10 µl of the PCR product was run on acrylamide gels (10%). 50 µl of the original sample was used for slot blot hybridization analysis.
Results:
The ethidium stained gel of the PCR product indicated that sonication did not release sufficient target DNA to allow it to be amplified by PCR and detected on the gel. The autoradiogram of the blot showed that no DNA hybridized to the radioactive probe and therefore sonication treatment alone released no DNA from the *M. tuberculosis*.

EXAMPLE 3

Procedure
3 ml pellets of BACTEC *Mycobacteria tuberculosis* cultures were prepared in substantial
accordance with the teachings of Example 1.

The sample was reconstituted in 0.5 ml $H_2O$ plus 25 µl worth of glass beads. The sample was then placed in a boiling water bath for 15 minutes with beads.

The lysed sample underwent 2 phenol/chloroform extractions then 2 chloroform/isoamyl alcohol extractions. These were followed by ethanol precipitation overnight at $-20°$ C. Sample was reconstituted in 150 µ$H_2O$. PCR mixes were set up, each using 50 µl of the lysate product and then cycled. 10 µl of the PCR product was run on acrylamide gels (10%). 50 µl of the original sample was used for slot blot hybridization analysis.
Results:
The ethidium stained gel of the PCR product indicated that heating in the presence of glass beads released sufficient target DNA to allow it to be amplified by PCR and detected on the gel and the level of amplification appeared to be the same as that done in the absence of glass beads. The autoradiogram of the blot showed that no DNA hybridized to the radioactive probe and therefore heat treatment plus glass beads did not release enough DNA to be detected or the DNA remained bound to the beads. Addition of the beads was considered to not be advantageous to the process of DNA release.

EXAMPLE 4

Procedure 3 ml pellets of BACTEC *Mycobacteria tuberculosis* cultures were prepared in substantial accordance with the teachings of Example 1.

The sample was reconstituted in 0.5 ml of $H_2O$ plus ~25 μl worth of glass beads. Sample was sonicated with the beads at 60° C. for 15 minutes.

The lysed sample underwent 2 phenol/chloroform extractions then 2 chloroform/isoamyl alcohol extractions. These were followed by ethanol precipitation overnight at −20° C. Sample was reconstituted in 150 μl $H_2O$. PCR mixes were set up, each using 50 μl of the lysate product and then cycled. 10 μl of PCR product was run on acrylamide gels (10%). 50 μl of the original sample was used for slot blot hybridization analysis.

Results:

The ethidium stained gel of the PCR product indicated that sonication with glass beads released target DNA which was amplified by PCR and detected on the gel. However, the level of amplified target observed was less than for the previous successful treatments in Examples 1 and 3. The autoradiogram of the blot showed that no DNA hybridized to the radioactive probe and therefore sonication plus glass beads did not release enough DNA to be detected or the DNA remained bound to the beads.

EXAMPLE 5

Procedure 3 ml pellets of BACTEC *Mycobacteria tuberculosis* cultures were prepared in substantial accordance with Example 1.

The sample was diluted into 200 μl of $H_2O$ then placed in GEN-PROBE lysing tube which was sonicated at 60° C. for 15 minutes then 300 μl additional $H_2O$ was added to the tube.

The lysed sample underwent 4 phenol/chloroform extractions then 2 chloroform/isoamyl alcohol extractions. These were followed by ethanol precipitation overnight at −20° C. Samples were reconstituted in 150 μl $H_2O$. PCR mixes were set up, each using 50 μl of the lysate product and then cycled. 10 μl of the PCR product was run on acrylamide gels (10%). 50 μl of the original sample was used for slot blot hybridization analysis.

Results:

The ethidium stained gel of the PCR product indicated that the Gen-Probe lysis method did release sufficient target DNA to allow it to be amplified by PCR and detected on the gel and the level of amplification appeared to be similar to be levels observed in Examples 1 and 3. The autoradiogram of the blot showed that DNA hybridized to the radioactive probe indicating that enough DNA was released to be detected. While Gen-Probe was successful, two extra phenol/chloroform extractions were required to clear the sample (i.e. remove contaminants from the lysis solution) before it was subjected to analysis.

EXAMPLE 6

Procedure:

10 μl of $10^6$/ml BACTEC-cultured *Mycobacteria tuberculosis* was placed in 1 ml of sterile $H_2O$ and from this solution 10 μl aliquots were placed in 0.6 ml tubes (=100 organisms/experiment). Each tube received 100 μl of 1 X PCR buffer and was incubated for 0, 1, 5, 10, and 15 minutes at 100° C. Following heating, the mixtures containing *Mycobacteria tuberculosis* were centrifuged for 5 minutes in a microcentrifuge (12,000× g) and the pellets and supernatants were subjected to PCR amplification using primers specific for the IS6110 *Mycobacteria tuberculosis* insertion element according to the following thermocycling protocol: 94° C. 3 min denature, then 94° C. 1 min denature, 62° C. 1 min anneal, 72° C. 1 min extension for 30 cycles, then 72° C. 7 min extension, and 4° C. soak. The amplified products were analyzed on ethidium-stained polyacrylamide gels.

Results:

It was found that all of the heating times produced lysis as shown by production of amplified target; including the 0 time (i.e., no boiling) control. Though initially surprising, this is consistent because the first temperature cycling of the PCR reaction consisted of heating to 94° C. for 3 minutes which appeared to suffice for *Mycobacteria tuberculosis* lysis as evidenced by amplified target. With increased period of heating from 1 to 15 minutes there was a reduction in the signal of amplified target in the pellets, which is consistent with the idea that the heat produced lysis of the organisms and therefore they were not pelleted by centrifugation.

It was concluded that the 94° C. heating produced during the thermocycling reaction was adequate to release amplifiable target DNA from the *Mycobacteria tuberculosis* and that increased incubation with 100° C. prior to the reaction produced increased lysis of *Mycobacteria tuberculosis.*

EXAMPLE 7

Procedure:

Further evidence suggested that 94° C. heating produced during the thermocycling reaction was adequate to release amplifiable target DNA from *Mycobacteria tuberculosis.* One hundred *Mycobacteria tuberculosis* organisms were put directly into a PCR mixture and subjected PCR cycling as described above. A positive control, consisting of 100 copies of plasmid SK4.3 which contains the 1S6110 sequence was run concurrently with a negative control which consisted of $H_2O$.

Results:

The amplified targets were analyzed on an ethidium-stained polyacrylamide gel. The positive control containing the 1S6110 sequence showed an amplified target while the intact organisms also showed an amplified target but which was about 10 fold stronger in intensity than the positive control which was consistent with the published observation that each *Mycobacteria tuberculosis* organism contains about 10 copies of the 1S6110 target sequence.

This experiment corroborated the previous conclusion that the 94° C. heating produced during the thermocycling reaction was adequate to release amplifiable target DNA from the *Mycobacteria tuberculosis.*

EXAMPLE 8

Purpose

Identify compatible buffers that, when mycobacteria are heated in a boiling water bath in their presence, will:

A. Lyse and release their DNA.

B. Allow this DNA to be amplified.

MATERIALS

BACTEC *M. tuberculosis* Culture Bottle (~$10^6$ orgs/ml)
BACTEC *M. Fortuitum* Culture (~$10^8$ orgs/ml)
NaCl (Fisher#5271-500 Lot#896394)

Na Phosphate (Fisher#5381 Lot#742308)
Na₃ Phosphate (Fisher#5377 Lot#78758)
10 X TBS pH 8.1 (+2% Azide)
Acetone (Fisher A18–000 Lot#902245)
10% SDS solution (BRL#5553JA Lot#ARU602)
NP-40 (Sigma#N-6507 Lot#36F-0198)
Tween 20 (BioRad Cat#170-0531 Control#M1419)
Achromopeptidase (Sigma#A-7550 Lot#127F-68391)
Trizma 9.0 (100 mM Tris 9.0 +10 mM NaCl)
10 X PCR Buffer (100 mM Tris pH 8.8, 500 mM KCl, 15 mM $MgCl_2$)
10 X REACT 6(1×50 mM NaCl, Tris, KCl+6 mM $MgCl_2$)

PROCEDURE

Fourteen 1.5 ml screw capped tubes were lined up. To each one, the pellet from 2 ml of *M. tuberculosis* culture was added. This was also performed with a culture of *M. Fortuitum*.

The following solutions were prepared in sterile $H_2O$:
1. Sterile $H_2O$
2. 100 mM NaCl
3. 1 X TBS (50 mM Tris-HCl, 150 mM NaCl pH 8)
4. 1 X PBS (50 mM $Na_2$ Phosphate, 150 mM NaCl pH 8)
5. 1 X PCR Buffer
6. 1 X React 6 (50 mM Tris-HCl pH12, NaCl, KCl+6 mM $MgCl_2$)
7. Trizma 9.0
8. Trizma 9.0+Achromopeptidase
9. 10% Acetone
10. 0.5% Tween 20
11. 0.5% NP-40
12. 0.5% SDS
13. Sodium phosphate (50 mM pH 12)
14. Sodium phosphate (50 mM pH 5)

300 μl of a solution was added to its appropriate mycobacteria pellet (1 Tb., 1 Fortuitum each) and incubated at 100° C. after vortexing for 30 minutes, except #8. #8 received 300 μl trizma 9.0 plus 36 μl of a 5 mg/ml solution of Achromopeptidase (50 units). This was incubated at 50° C. for 30 minutes, then at 100° C. for 30 minutes. All samples were phenol/chloroform extracted, then chloroform extracted, and then ethanol precipitated overnight.

Samples were reconstituted into 30 μl of sterile water, then 15 μl of sample plus 5 μl of Type II tracking dye was electrophoressed on 1% Agarose gel in 1 X TAE and visualized after ethidium bromide staining. 5 μl of each sample (Tb only) was placed into PCR mixes, containing 0.25uM of M.Tb. 21 and 22 primers, as well as 2.5 units amplitaq polymerase. Samples were cycled as follows:

| 94° C. | 3 minutes | Denature | |
|---|---|---|---|
| 94° C. | 1 minute | Denature | |
| 62° | 1 minute | Anneal | } 30 cycles |
| 72° C. | 1 minute | Extension | |
| 72° C. | 7 minutes | Extension | |
| 4° C. | | Soak | |

10% of each PCR product was electrophoressed on 10% acrylamide gels and ethidium bromide stained.

RESULTS

The agarose gel results indicate that the *M. Fortuitum* samples, which have 100 times more organisms, release more (quantity wise, not percentage wise) DNA than *Mycobacteria tuberculosis*. For *Mycobacteria tuberculosis*, DNA is seen in achromopeptidase/boiled, the Tween 20/boiled sample, and 0.5% SDS.

The PCR results show that all solutions cause (*Mycobacteria tuberculosis*) DNA to be released upon boiling, except SDS which is known for inhibiting PCR.

CONCLUSIONS

This data shows that 13 of the 14 solutions tested will liberate *Mycobacteria tuberculosis* DNA when boiled in such amounts that PCR can detect it. The agarose gel shows that the buffers liberate small-sized DNA from *M. Fortuitum*, but not enough organisms were present of *M. tuberculosis* to allow much DNA to be seen on the gel.

EXAMPLE 9

Lysis of Mycobacteria by Forced Hot Air Heating at 100° C.

A. Materials and Methods

The following mycobacteria species were used in this Example:

| Organism | Source/Strain |
|---|---|
| M. avium | ATCC 25291 |
| M. chelonei | Trudeau Society 1542 |
| M. fortuitum | Trudeau Society 1529 |
| M. gordonae | Trudeau Society 1318 |
| M. intracellulare | ATCC 13950 |
| M. kansasii | Trudeau Society 1201 |
| M. thermoresistible | CAP Survey⁺ |
| M. tuberculosis | Trudeau Society 201 |
| M. xenopii | Trudeau Society 1482 |

⁺CAP = College of American Pathologists

All organisms were grown on Lowenstein-Jensen (LJ) slants and in Bactec 12B vials (Becton Dickinson Diagnostic Instrument Systems, Towson, Md). The concentration of organisms was adjusted to the various McFarland standards by dispersing organism clumps with glass tissue grinders and diluting with a 25 mM potassium phosphate buffer, pH 7.6.

Viability of the organisms in the killing phase of the Example was determined by culturing 0.2 ml of the suspensions in Bactec 12B vials with PANTA solution (Becton Dickinson) for at least six weeks at 37° C. All positive Bactec signals were confirmed by acid fast stains (Kinyoun's and Auramine O) and gram stain. Vials with questionable results were subcultured onto blood agar and LJ slants. Growth on LJ slants incubated at 37° C. in $CO_2$ was also used as an adjunct to the Bactec system for certain experiments. Organism concentration was determined by the pour plate method with Middlebrook 7H10 agar (Difco, Detroit, Mich.).

Clinical samples were processed by the n-acetyl cysteine-NaOH method (Remel, Lenexa, Kans.) and resuspended in 1 ml of 0.2% bovine albumin (Remel). The resulting suspension is referred to as a "NALC pellet" below.

1. Heating of Mycobacteria

First, 1.5 and 4.5 ml volumes of McFarland 2 suspensions of all organisms listed in Table 1 except *M. bovis* were heated at 100° C. in a boiling water bath, and samples were taken at 0, 5, 10, 15 and 30 minutes. In three separate experiments, no mycobacteria species grew after being heated at 100° C. for at least 5 minutes.

However, due to inherent safety problems associated with a boiling water bath, the 100° C. heating experiments were repeated using a forced heat air oven. The results with the forced hot air oven were identical to that of the boiling water bath. Also 7 positive and 7 negative NALC pellets from clinical samples were heated in the forced hot air oven at 100° C. for 30 minutes. None of these heated NALC pellets were positive after 6 weeks incubation.

2. PCR Amplification

PCR amplification of *M. tuberculosis* target DNA after heat killing was performed according to standard protocol (Saiki, R. K. et at., *Science* 230, 1350 (1985)) using primers specific for the region between nucleotides 956 and 1029 of the IS6110 *M. tuberculosis* complex insertion element as described in Thierry, D. C. et al., *Mol. Cell. Probes* 6, 181 (1992). PCR amplifications of mycobacterial genus DNA used primers specific for a sequence within the 65K gene as described by Shinnick, T. M. et al., *Infec. Immun.*, 56,446 (1988). Briefly, each reaction contained 50 µl of PCR buffer mix comprised of 20 mM Tris-HCl, pH 8.8, 100 mM KCl, 4.5 mM $MgCl_2$, 1.0 mM deoxynucleotide triphosphates, 20 mM 2-mercaptoethanol with freshly added primers (50pM) and Taq polymerase (2.5 units; Cetus Perkin-Elmer, Branchburg, N.J. This was added from a premixed stock solution into a 0.5 ml microfuge tube containing 50 µl of sample and overlain with approximately 50 µl of mineral oil (Sigma, St. Louis, Mo.

a. Temperature cycling protocols:

For amplification of IS6110 the PCR mixture was incubated in a model 480 temperature cycler (Cetus Perkin-Elmer) set for one 3 minute denaturation cycle at 94° C., and thirty cycles consisting of 1 minute denaturation at 94° C., 1 minute annealing at 62° C., 1 minute extension at 72° C. This was followed by a 7 minute extension step at 72° C.

Amplification of the 65K target was performed in a model 480 temperature cycler (Cetus Perkin-Elmer) set for one 3 minute denaturation cycle at 95° C., and twenty seven cycles consisting of 1.5 minute denaturation at 95° C., 1 minute annealing at 50° C., 2 minute extension at 72° C. This was followed by a 7 minute extension step at 72° C.

b. Detection of PCR Amplified DNA

PCR products were visualized by electrophoresis on 10% polyacrylamide gels and stained with ethidium bromide. Products were quantified by a chemiluminescent solid phase sandwich assay or by densitometry of Polaroid photographs (type 57 film) of the ethidium bromide stained gels on a SciScan 5000 scanning densitometer (U.S. Biochemical, Cleveland, Ohio).

3. SDA Amplification

Isothermal amplification of mycobacterial DNA after heat killing by SDA was performed by the method of Walker et al., *Proc. Nat'l. Acad. Sci. USA* 89, 392 (1992) and *Nuc. Acids Res.* 20, 1695 (1992) using an IS6110 DNA target for *M. tuberculosis* and a 16s rDNA for the Mycobacterium species. 25 µl of sample were mixed with 20 µl of solution 1 (described below) in a 0.5 ml microfuge tube, then denatured in a boiling water bath for 2.5 minutes. After cooling to 41° C. in a heat block (USA/Scientific Thermolok Dry Bath, Ocala, Fla.), 5 µl of solution 2 (described below) was added. The tubes were incubated at 41° C. for 2 hours after which the SDA reaction was terminated by incubating for 2 minutes in a 95° C. heating bath. SDA products were detected by a chemiluminescent solid phase sandwich assay. To control for the effects of inhibitors synthetic target sequences were added to each reaction vial.

a. IS6110 amplification

Solution 1. 17.5 mM $MgCl_2$, 0.25mg/ml bovine serum albumin, 22.5 glycerol, 90.75 mM $KPO_4$, 0.5 mM deoxy- nucleotide triphosphates (dGTP, dTTP, dCTP), 0.5 mM deoxadenosine 5'-[α-thio]triphosphate and 1250 nM of each of the four primers B1, B2, S1, and S2 which are published in Walker, G. T. et al. (1994) A Chemiluminescent DNA probe test based upon strand displacement amplification. *Viral Detection Methods*. Academic Press, and 250 ng of ultrapure human placental DNA (Sigma) in $H_2O$. The $MgCl_2$ was carefully added last to avoid precipitation of $MgPO_4$, 25,000 copies of the synthetic control sequence of the same Walker et al. publication were included in each reaction.

Solution 2. HincII restriction endonuclease and exo-Klenow fragment of Polymerase I were diluted with $H_2O$ to the respective specific activities of 150 and 3 units per 5 µl.

16S amplification

Solution 1. =0.25mg/ml bovine serum albumin, 30% Dimethly sulfoxide (DMSO), 81.25 mM $KPO_4$, 1.25 mM deoxynucleotide triphosphates (dGTP, dTTP, dCTP), 0.5 mM deoxyadenosine 5'-[α-thio]triphosphate and 1250nM of each of the four primers B1, B2, S1, S2 and 250 ng of ultrapure human placental DNA (Sigma) in $H_2O$. 500 copies of the synthetic control sequence were included in each reaction. As with the IS6110 amplification discussed above, the primers and control sequence used in this 16S amplification are published in the Walker et al. reference.

Solution 2.=HincII restriction endonuclease and exo-Klenow fragment of

Polymerase I were diluted with $H_2O$ to the respective specific activities of 150 and 3 units per 5 µl as for the IS6110 amplification and magnesium acetate was added to a concentration of 65 mM.

B. Assay detection of amplified DNA.

1. IS6110

PCR and SDA amplified *M. tuberculosis* IS6110 DNA was detected by solution phase hybridization of a biotinylated DNA probe disclosed in the Walker et al. publication and an alkaline phosphatase-conjugated detector probe disclosed in the Walker et al. publication specific to the internal sequence of the amplification products.

2. 16S rDNA

SDA amplified mycobacterial 16S DNA was detected with a biotinylated capture probe and two alkaline-phosphatase conjugated detector probes, while the amplified internal control was captured by a different set of capture and detector probes. All of these capture and detector probes are disclosed in the Walker et al. publication.

Hybridization was performed for 45 minutes at 37° C. in a streptavidin-coated microtiter plate (Microlite 1, Dynatech, Chantilly, Va.) containing 100 mM Tris-HCl, pH 7.0, 1.8 M NaCl, 0.2% acetylated bovine serum albumin, 0.1 mM $ZnCl_2$, 0.1% $NaN_3$. The plates were then washed three times (300 µl/wash) with 100 mM Tris-HCl, pH 7.5, 250 mM NaCl, 0.1% bovine serum albumin and 0.1% $NaN_3$ to remove unbound biotinylated probe. A chemiluminescent alkaline phosphatase substrate, Lumi-Phos 530 (Lumigen, Southfield, Mich.), was added to the wells and incubated for 30 minutes at 37° C. The reactions were then read in a luminometer (Labsystems Luminoscan, Finland).

C. Results

Genomic DNA from the samples of the heat killed organisms was subjected to amplification using PCR and SDA as described above. The amplification of genomic DNA shown in Tables III and IV below evidence the lysis of these mycobacteria species by exposure to 100° C. temperature for 30 minutes in a forced hot air oven.

TABLE III

PCR OF DNA FROM HEAT-LYSED MYCOBACTERIA SPECIES

| SPECIES | RDUs* |
|---|---|
| M. tuberculosis | 239.7 |
| M. intracellulare | 161.7 |
| M. avium | 177.0 |
| M. chelonei | 78.1 |
| M. thermoresistible | 92.5 |
| M. fortuitum | 192.7 |
| M. kansasii | 149.5 |
| M. gordonae | 40.4 |
| M. xenopi | 203.9 |
| Negative control | 4.7 |

*RDU = relative density unit

TABLE IV

SDA OF DNA FROM HEAT-LYSED MYCOBACTERIA SPECIES

| SPECIES | GENUS RLUs* | INTERNAL CONTROL RLUs |
|---|---|---|
| M. tuberculosis | 13058 | 1601 |
| M. intracellulare | 14027 | 1439 |
| M. avium | 8724 | 1028 |
| M. chelonei | 1306 | 1544 |
| M. thermoresistible | 1706 | 2247 |
| M. fortuitum | 3033 | 1083 |
| M. kansasii | 13947 | 942 |
| M. gordonae | 6992 | 3150 |
| M. xenopi | 689 | 1413 |
| Negative control | 27 | 3275 |

*RLU = relative light unit

Amplification of genomic DNA from the 7 positive clinical samples by PCR and SDA was also observed. However, results of amplification of the 7 negative clinical samples were consistent with the negative control.

Heating of mycobacteria in a forced hot air oven not only resulted in lysis of the mycobacteria but also non-viability or killing.

EXAMPLE 10

Lysis of Mycobacteria by Forced Hot Air Heating at 95° C. and 105° C.

Four mycobacterial species, M. tuberculosis, M. avium, M. chelonae and M. intracellulare were cultured in Bactec™ Media 7H9 for Mycobacteria. The cells were harvested just after entering logrythmic phase as indicated by GI (growth index). Therefore, the cells were considered viable, and there was less likelihood of complications from mycobacterial DNA being released from cells spontaneously due to cell breakdown after death.

Samples of all four mycobacterial species were subjected to heating in a forced hot air oven at: (1) 95° C. for 5, 10, 15 and 30 minute intervals; and (2) 105° C. for 5, 10, 15 and 30 intervals.

Target DNA for either IS6110 or Genus detection released from lysed mycobacteria was then amplified using the SDA methods described in Example 10. As shown in Table 2 below, amplifiable target DNA for IS6110 and Genus detection was released from all samples at both temperatures regardless of exposure time. Although sample number 20 appeared to have low amplification, this result was due to complications of the sample during amplification, not during cell lysis as indicated by the suppressed control sequence (signature).

TABLE 2

Amplification of Mycobacterial DNA After Lysis at 95° C. and 105° C.

| Sample # | Species | Temp. | Time | GI | IS6110 | Genus | Signature |
|---|---|---|---|---|---|---|---|
| 1 | tuberculosis | 95 C. | 5' | 70 | 77966 | 75105 | 7754 |
| 2 | " | 95 C. | 10' | | 74200 | 58006 | 10701 |
| 3 | " | 95 C. | 15' | | 77380 | 80744 | 9001 |
| 4 | " | 95 C. | 30' | | 77005 | 92741 | 13695 |
| 5 | " | 100 C. | 5' | 145 | 75987 | 69625 | 7518 |
| 6 | " | 100 C. | 10' | | 73237 | 78294 | 11218 |
| 7 | " | 100 C. | 15' | | 73023 | 75464 | 10455 |
| 8 | " | 100 C. | 30' | | 69722 | 74620 | 7993 |
| 9 | avium | 95 C. | 5' | 70 | 13 | 89191 | 4073 |
| 10 | " | 95 C. | 10' | | 10 | 88090 | 2598 |
| 11 | " | 95 C. | 15' | | 111 | 85086 | 1849 |
| 12 | " | 95 C. | 30' | | 11 | 90384 | 1603 |
| 13 | " | 100 C. | 5' | 133 | 96 | 91375 | 1350 |
| 14 | " | 100 C. | 10' | | 29 | 88899 | 2008 |
| 15 | " | 100 C. | 15' | | 19 | 85065 | 2194 |
| 16 | " | 100 C. | 30' | | 62 | 81745 | 1375 |
| 17 | chelonae | 95 C. | 5' | 201 | 9 | 41447 | 3598 |
| 18 | " | 95 C. | 10' | | 10 | 19953 | 4279 |
| 19 | " | 95 C. | 15' | | 98 | 46995 | 3309 |
| 20 | " | 95 C. | 30' | | 12 | 1144 | 108 |
| 21 | " | 100 C. | 5' | 473 | 15 | 21246 | 3483 |
| 22 | " | 100 C. | 10' | | 13 | 15795 | 3157 |
| 23 | " | 100 C. | 15' | | 16 | 16562 | 5124 |
| 24 | " | 100 C. | 30' | | 124 | 17235 | 2737 |
| 25 | intracellularae | 95 C. | 5' | 85 | 8 | 57191 | 5967 |
| 26 | " | 95 C. | 10' | | 13 | 79016 | 8331 |
| 27 | " | 95 C. | 15' | | 15 | 72134 | 8023 |
| 28 | " | 95 C. | 30' | | 21 | 80282 | 7436 |
| 29 | " | 100 C. | 5' | 127 | 20 | 86008 | 9670 |
| 30 | " | 100 C. | 10' | | 35 | 59088 | 3478 |
| 31 | " | 100 C. | 15' | | 335 | 78192 | 6858 |

TABLE 2-continued

| 32 | " | 100 C. | 30" | | 35 | 67761 | 4163 |
|---|---|---|---|---|---|---|---|

CONTROLS

SDA

| GENOMIC TARGETS | IS6110 | GENUS | SIGNATURE |
|---|---|---|---|
| 0 | 14 | 77 | 7002 |
| 10 | 2982 | 761 | 11939 |
| 20 | 6800 | 368 | 9902 |
| 40 | 17514 | 1503 | 13128 |

ASSAY

| LEVEL OF ATOM MOLES OF TARGET* | IS6110 | GENUS | SIGNATURE |
|---|---|---|---|
| 0 | 19 | 262 | 43 |
| LOW | 1198 | 1841 | 2613 |
| MED | 3979 | 7335 | 11273 |
| HIGH | 13779 | 20475 | 30486 |

*LOW = 500 for IS6110 and 2000 for Signature
MED = 2000 for IS6110 and 8000 for Signature
HIGH = 8000 for IS6110 and 32000 for Signature Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A process for lysis of Mycobacteriaceae wherein said lysis comprises exposing the Mycobacterium to a lysis effective amount of heat in the absence of lysogenic agents and other physical lysogenic conditions, and wherein said lysis effective amount of heat is provided as forced hot air and renders the Mycobacterium noninfectious.

2. The process of claim 1 in which the Mycobacteriaceae is selected from the group consisting of M. avium, M. intracellulare, M. gordonae, M. tuberculosis, M. kansasii, M. fortuitum, M. chelonae, M. bovis, M. scrofulaceum, M. paratuberculosis, M. phlei, M. marinum, M. simiae, M. scrofulaceum, M. szulgai, M. leprae, M. xenopi, M. ulcerans, M. lepraemurium, M. flavescens, M. terrae, M. nonchromogenicum, M. malmoense, M. asiaticum, M. vaccae, M. gastri, M. triviale, M. haemophilum, M. africanum, M. thermoresistable, and M. smegmatis.

3. The process of claim 2 in which the Mycobacteria is M. tuberculosis.

4. The process of claim 2 in which the Mycobacteria is M. bovis.

5. The process of claim 2 in which the Mycobacteria is M. africanum.

6. The process of claim 2 in which the Mycobacteria is M. intracellularae.

7. The process of claim 2 in which the Mycobacteria is M. avium.

8. The process of claim 2 in which the Mycobacteria is M. leprae.

9. The process of claim 2 in which the Mycobacteria is M. chelonae.

10. The process of claim 2 in which the Mycobacteria is M. paratuberculosis.

11. The process of claim 1 which further comprises isolation of cellular components.

12. The process of claim 11 in which the cellular component isolated is DNA.

13. The process of claim 11 in which the cellular component isolated is RNA.

14. The process of claim 1 which further comprises amplification of mycobacteria nucleic acid.

15. The process of claim 14 in which the nucleic acid is DNA.

16. The process of claim 14 in which the nucleic acid is RNA.

17. The process of claim 3 which further comprises the isolation of DNA.

18. The process of claim 4 which further comprises the isolation of DNA.

19. The process of claim 5 which further comprises the isolation of DNA.

20. The process of claim 6 which further comprises the isolation of DNA.

21. The process of claim 7 which further comprises the isolation of DNA.

22. The process of claim 1 which further comprises the addition of a Mycobacteria identifying agent.

23. The process of claim 22 in which the Mycobacteria identifying agent is a nucleic acid probe.

24. The process of claim 23 in which the nucleic acid probe is deoxyribonucleic acid.

25. The process of claim 23 in which the nucleic acid probe is ribonucleic acid.

26. The process of claim 1 in which the Mycobacteria is obtained from a source selected from the group consisting of feces, sputum, blood, tissue, urine, and other body fluids.

* * * * *